United States Patent
Jonckers et al.

[11] Patent Number: 6,165,315
[45] Date of Patent: Dec. 26, 2000

[54] REACTOR FOR THE SYNTHESIS OF UREA

[75] Inventors: Kees Jonckers, Susteren; Hendrik F. Perrée, Maastricht, both of Netherlands

[73] Assignee: DSM N.V., Heerlen, Netherlands

[21] Appl. No.: 09/303,687

[22] Filed: May 3, 1999

Related U.S. Application Data

[63] Continuation of application No. 08/993,871, Dec. 18, 1997, abandoned, which is a continuation of application No. 08/405,623, Mar. 15, 1995, abandoned.

[51] Int. Cl.$^7$ .......................... C07C 273/02; B01J 10/00
[52] U.S. Cl. ...................... 159/47.2; 202/158; 261/114.3; 422/193; 564/67
[58] Field of Search ........................... 422/193, 188–189, 422/148, 236, 311; 261/114.3, 114.1, 112.2; 202/158; 159/47.2; 564/67, 69–70, 73; 203/49, 87

[56] References Cited

U.S. PATENT DOCUMENTS

| | | | |
|---|---|---|---|
| 2,857,431 | 10/1958 | Glass et al. | 261/114.1 |
| 2,973,189 | 2/1961 | Chu | 261/114.1 |
| 3,046,307 | 7/1962 | Bochinski | 564/70 |
| 3,143,482 | 8/1964 | McLeod et al. | 261/114.1 |
| 4,098,579 | 7/1978 | Starzycki et al. | 422/193 |
| 4,341,640 | 7/1982 | Landis | 210/752 |
| 4,356,132 | 10/1982 | Belyakov et al. | 261/114.1 |
| 4,539,077 | 9/1985 | Jonckers et al. | 203/49 |
| 4,942,066 | 7/1990 | Fan et al. | 427/54.1 |
| 5,002,855 | 3/1991 | Fan et al. | 425/162 |
| 5,223,238 | 6/1993 | Czuppon | 423/359 |
| 5,304,353 | 4/1994 | Dente et al. | 422/193 |
| 5,888,460 | 3/1999 | Zardi et al. | 422/193 |

FOREIGN PATENT DOCUMENTS

| | | |
|---|---|---|
| 2141886 | 3/1995 | Canada. |
| 13224 | 1/1985 | European Pat. Off.. |
| 487 935 | 6/1992 | European Pat. Off.. |
| 1953994 | 5/1970 | Germany. |
| 45-38813 | 12/1970 | Japan. |
| 818864 | 8/1959 | United Kingdom. |
| 1202316 | 10/1972 | United Kingdom. |
| WO 95/31278 | 11/1995 | WIPO. |
| WO96/41239 | 12/1996 | WIPO. |

OTHER PUBLICATIONS

Declaration of Henrik F. Perree, Jun. 3, 1997.

*Primary Examiner*—Hien Tran
*Attorney, Agent, or Firm*—Pillsbury Madison & Sutro, LLP Intellectual Property Group

[57] ABSTRACT

A reactor for the synthesis of urea from ammonia and carbon dioxide at elevated temperature and pressure is provided with perforated reactor trays in which at least a pair of spaced part perforated reactor trays each have at least one opening at least a distance closer towards the periphery than the center, such as on or near the edge of a perforated reactor tray, and each of such pair perforated reactor trays is provided with a tube with a height of 50–500 mm located on and depending from an underside, e.g. bottom side in a column reactor, of each of such pair perforated reactor tray. The tubes extend to no more than $\frac{1}{3}$ of the distance between two adjacent reactor trays.

8 Claims, 4 Drawing Sheets

REACTOR FOR THE SYNTHESIS OF UREA

This application is a continuation of U.S. application Ser. No. 08/993,871, filed on Dec. 18, 1997, now abandoned which is itself a continuation of U.S. application Ser. No. 08/405,623, filed Mar. 15, 1995, now abandoned.

FIELD OF THE INVENTION

This invention relates to an improved reactor for the synthesis of urea from ammonia and carbon dioxide at elevated temperatures and pressures.

BACKGROUND OF THE INVENTION

It is well known that, when ammonia and carbon dioxide are subjected to high temperature in a closed system, high pressures are generated and urea is formed. In general, urea and urea synthesis are described in *Encyclopedia of Chemical Technology*, 23: 548–575 (1983) including the references cited therein, the complete disclosures of which are incorporated herein by reference.

Urea synthesis has been conducted at pressures of from about 100–350 atmospheres in an autoclave maintained at temperatures of 125–250° C. During the synthesis reaction, the ammonia and carbon dioxide combine exothermically to form ammonium carbamate which is then converted into urea and water. In addition to urea and water, the resulting reaction mixture contains uncombined residues of the starting materials and ammonium carbamate. The carbon dioxide and ammonia, which are introduced to the autoclave under pressure, are in either a liquid or vaporous state, while the water, formed during dehydration of ammonium carbamate to urea, forms an absorbent for the ammonia and carbon dioxide. The dehydration reaction takes place in the liquid phase. The conversion of reactants to urea is only partial because of the equilibrium of the dehydration reaction.

The yield of urea from a high pressure synthesis reactor will be appreciably higher, if in passing through the reaction space in a reactor, the liquid phase is passed through the autoclave by plug-flow sometimes referred to as ("piston flow"). The contact between the gaseous phase and the liquid phase results in the condensation of at least part of the gaseous phase. The condensation heat which is recovered, is used for dehydrating the ammonium carbamate to urea.

It has been found that to accomplish the above, the reaction space in a cylindric reactor is subdivided by a plurality of vertically spaced, horizontally disposed perforated reactor trays as is described in, for instance, U.S. Pat. No. 3,046,307, the complete disclosure of which is incorporated herein by reference. With these reactor trays partitioning the inner volume of the reactor, a plurality of compartments or zones is formed, that are consecutively arranged along the direction of the flow of the reaction mixture. Such reactor trays are preferably arranged horizontally within the reactor and cause a uniform mixing of reaction components in each of the zones formed therebetween. The state of the art perforated reactor trays extend horizontally over the entire cross section of the reactor and each contains a plurality of orifices for the passing of the two-phase gas and liquid flow. Since the liquid and gaseous phases pass through the same orifices, the gas flow relative to the liquid flow passing through these orifices is ill-defined, and results in unpredictable random flow patterns of gas and liquid. As a result 'stagnant zones' may well be expected in certain areas in a compartment, resulting in a lower conversion.

Another representative means for subdividing the reactor space in a urea synthesis reactor is to use reactor trays with an annular opening between the perforated reactor trays and the internal wall of the reactor as depicted in FIG. 1. Through this annular opening mainly transportation, e.g. fluid flow, of the liquid phase occurs whereas the transportation, e.g. fluid flows of the gaseous phase occurs through in the central portion perforations of each reactor tray. Although the liquid velocity in this annular opening is relatively low, it is possible that part of the liquid flows along the wall to the top of the reactor without being mixed with the bulk of the liquid. This phenomenon is called 'bypassing' and is responsible for a smaller conversion of ammonium carbamate into urea compared with that theoretically possible.

Another phenomenon that is responsible for a reduced conversion is 'backmixing'. This happens when a liquid flows from an upper compartment to a lower compartment e.g. via the perforations, as seen, for example, in U.S. Pat. No. 4,098,579, the complete disclosure of which is incorporated herein by reference. In the case of backmixing the plug-flow behavior is not optimal and there is an appreciable negative influence on the theoretically obtainable urea yield.

A further increase in urea yield is said to be obtainable by providing urea synthesis reactors with perforated reactor trays with at least one opening for liquid flow on the edge of the perforated reactor tray. These openings for the liquid flow in two adjacent perforated reactor trays are located opposite the central part of the reactor in order to force the liquid flow to pass the central part of the reactor where the transport of the gaseous phase takes place as is demonstrated in Japanese Patent Publication (Kokai) A-38813 (1970), the complete disclosure of which is incorporated herein by reference. In this way a substantially zigzag flow path of the liquid is created which crosses the substantially vertical flow path of the gaseous phase. In this way bypassing is said to be avoided and the urea yield is said to be improved.

SUMMARY OF THE INVENTION

It is an object of this invention to provide an improved reactor for the conversion of reactants to urea whereby such conversion may approach more nearly to that theoretically possible.

It is also an object of this invention to provide an improved reactor tray in order to overcome the negative influence on the maximum attainable conversion caused by backmixing, bypassing and stagnant zones behaviour.

Another object of this invention is to increase the yield of urea from a high pressure-high temperature synthesis reaction while at the same time increasing the rate of through-put of reactant materials.

A further object of the invention is to provide a means for facilely retrofitting, or modernizing reactors, and particularly urea reactors and hydrolyzers.

Yet another object of this invention is a reactor for carrying out the pressure synthesis of urea whereby an appreciable reduction in apparatus volume is realized without a reduction in the rate of through-put of reactant materials or decrease in yield of urea.

These and other objects can be achieved by providing a reactor (or hydrolyzer) with perforated reactor trays each of which is provided with at least one liquid riser at or proximate to the edge of each perforated reactor tray whereby the liquid risers in two adjacent perforated reactor trays are not in direct axial alignment with one another, but are opposingly located relative to one another as well as the central part of the reactor. In a preferred embodiment, these liquid risers are provided with a hollow tube extending from the bottomside of the perforated reactor trays. The hollow tubes have a height of 50–500 mm relative to the bottom or side whereby the tubes extend to no more than ⅓ of the distance between two adjacent reactor trays. As evident, it is not preferred that the openings in liquid risers in adjacent trays are stacked immediately spaced one on top of the another. By preference, the reactor is a vertically disposed cylinder (or "column") urea synthesis reactor for the synthesis of urea from ammonia and carbon dioxide at elevated temperature and pressure.

DETAILED DESCRIPTION OF THE INVENTION

Figure 1:
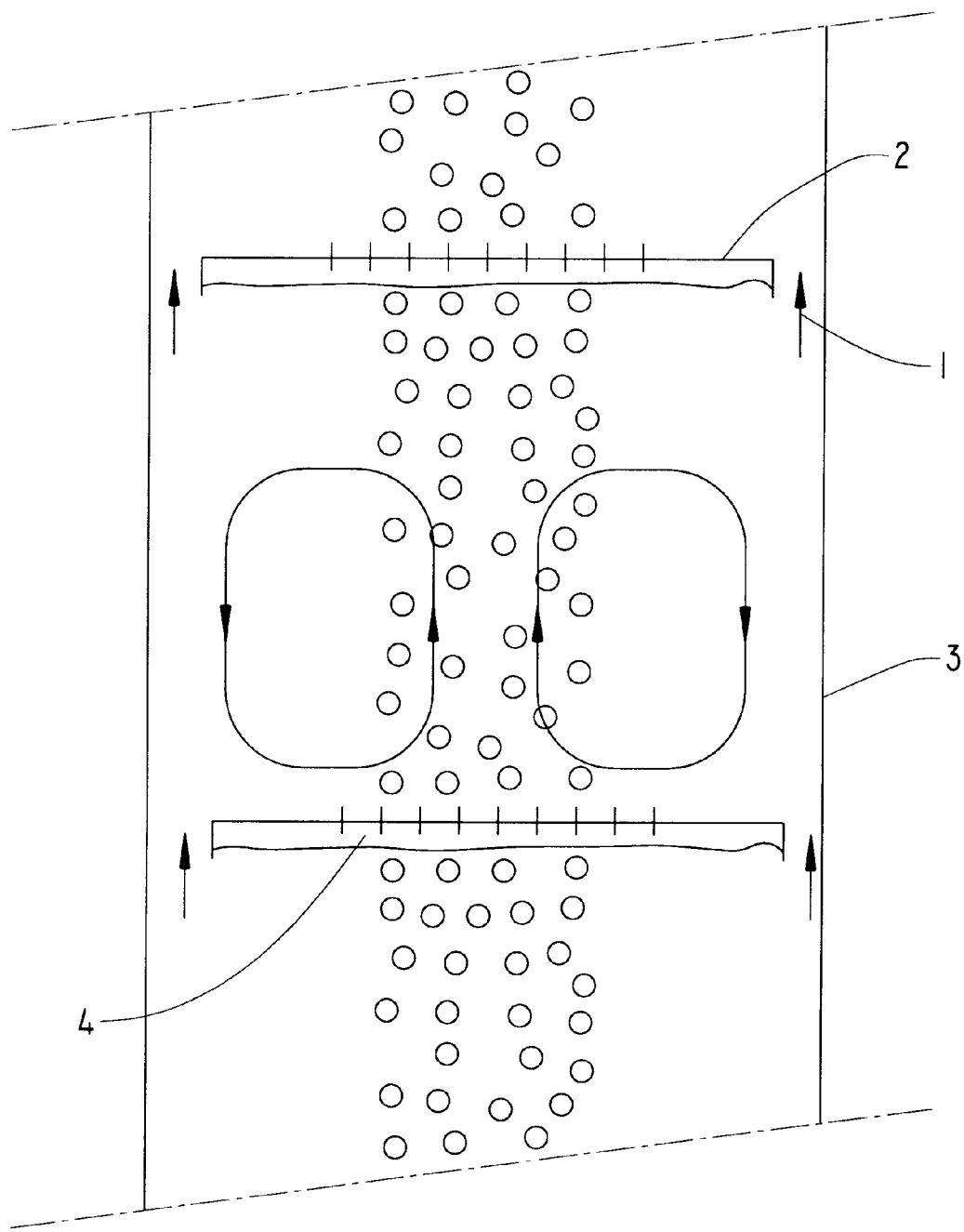
FIG. 1 is a longitudinal cross section view of a part of a conventional urea reactor.

It is advantageous to partition at least a portion of the internal volume enclosed by a urea synthesis reactor with perforated reactor trays wherein the partitioning is with at least a pair of perforated reactor trays, such that each tray has at least one liquid riser (opening or passage or orifice), and may have for example two liquid risers, at least at a locus closer towards the periphery than the center, such as on or near the edge of a perforated reactor trays, and each liquid riser in such pair perforated reactor trays includes a hollow tube with a height of 50–500 mm located on and depending from an underside, e.g. bottom side in a column reactor, of each of such pair perforated reactor trays, and wherein one end of the hollow tube is unconnected but open to a compartment or zone bounded by the pair adjacent perforated trays, and the other open end of the hollow tube is integral with and circumscribes an opening of equal shape as the hollow tube in a perforated tray, but the openings of liquid risers in adjacent trays are not one immediately on top of the other. By preference, each tube in each liquid riser has a height of 100–300 mm relative to the plane defined by the underside of a reactor tray. In general, a tube extends to no more than ⅓ of the distance between two adjacent reactor trays and by preference to no more than ¼ of that distance.

It has been found that the distance between the individual reactor trays can be between 500 and 5000 mm at substantially equal distances. By preference, the reactor trays are at least substantially parallel to one another.

A liquid riser includes an opening or orifice in a reactor tray for liquid transport, and the opening (as can be the tube extending therefrom) can be of a circular, ellipsoidal or polygonal shape. By present preference the openings can have the same geometric shape. In general, the planar cross-sectional area of the opening for liquid flow through a liquid riser is such that the liquid velocity in the liquid riser is between 0.05 to 1 m/sec, preferably 0.10 to 0.60 m/sec and more preferably 0.10 to 0.30 m/sec. In practice, this means for a urea synthesis reactor the at least one liquid riser has a cross-sectional area between 1 and 10% of the surface of the perforated reactor tray.

It has further been found that a minimum velocity of the gaseous phase as it passes through the perforations of at least 2.5 m/sec is preferred in order to obtain an effective separation of the liquid in two adjacent compartments or zones of the reactor. This velocity can range from 2.5 to 10 m/sec, more particularly it can range from 2.5 to 5 m/sec, and is typically about 3 m/sec. In this way backmixing is avoided and the urea yield will nearly approach the theoretically possible urea yield. In order to obtain this velocity in a given reactor, the perforations (in number and diameter) should be selected to result in this velocity. The number, size and distribution of perforations can, if desired be varied between reactor trays. The minimum size for e.g. circular perforations is 2 mm, more particularly 2 to 20 mm, although by present preference the range is 5 to 10 mm. The perforations for the transport of the gaseous phase are by preference located in the center of the reactor tray over 20 to 80% of the surface of the reactor tray and more particularly over 40 to 60% of the surface. The perforations in a given tray are spaced apart from, and separated the at least one liquid riser to avoid mixing, flow and other problems. Thus, for instance, a liquid riser can be at or proximate to the outer edge of a reactor (or hydrolyzer) tray, whereas the perforations are in the central area or region of a tray.

The invention is in particular suitable for a process for the synthesis of urea at a temperature below 200° C. such as 160° C. to 200° C. and a pressure of below 200 bar such as 120 bar to 195 bar. By preference the pressure in the reactor is between 120 and 175 bar.

This invention can also be used for other reactions where plug-flow of the liquid phase accompanied by liquid/gas contact takes place such as urea hydrolysis at high temperature and pressure. In these reactions urea is removed from a liquid phase containing urea by hydrolysis of the urea at high temperature and pressure. This can be done by partitioning at least a portion of the internal volume enclosed by a urea hydrolyzer with perforated hydrolyzer trays in which a pair of adjacent perforated hydrolyzer trays each have at least one liquid riser (including an opening in the tray), and for example two liquid risers, at least a locus closer towards the periphery than the center, such as on or near the edge of a perforated hydrolyzer tray, and each of such pair adjacent perforated hydrolyzer trays is provided with a tube with a height of 50 to 500 mm located on and depending from an underside, e.g. bottom side in a column hydrolyzer, of each of such pair adjacent perforated hydrolyzer trays and wherein one end of the hollow tube is open to the compartment or zone bounded by the pair adjacent perforated trays, and the other open end of the tube is integral with and circumscribes a like shaped opening in a perforated tray, but the opening of liquid risers in adjacent trays are not stacked one immediately on top of the other. By preference, a tube has a height of 100 to 300 mm relative to the plane defined by the underside of a hydrolyzer tray. The tubes extend to no more than ½ of the distance between the adjacent hydrolyzer trays and by preference to no more than ¼ of that distance.

It has been found that the distance between the individual hydrolyzer trays can be between 300 mm and 3000 mm, and by preference the hydrolyzer trays are spaced apart from one another at a substantially equal distance.

An opening in a hydrolyzer tray for liquid transport (liquid riser) can be of a circular, ellipsoidal or polygonal shape, although by present preference the openings can have the same geometric shape. In general, the planar cross-sectional area of the opening in a liquid riser for liquid flow is such that the liquid velocity in the liquid riser is between 0.05–1 m/sec, preferably 0.10 to 0.60 m/sec and more preferably 0.10 to 0.30 m/sec. This means in practice for a urea hydrolyzer a cross-sectional area of a liquid riser or liquid risers between 1 and 10% of the surface of the perforated hydrolyzer tray.

It has further been found that a minimum velocity of the gaseous phase as it passes through the perforations of at least 4.0 m/sec is preferred in order to obtain an effective separation of the liquid in two adjacent compartments or zones of the hydrolyzer. This velocity can range from 4.0 to 25 m/sec more particularly it can range from 4.0 to 15 to m/sec. In order to obtain this velocity in a given hydrolyzer, the perforations (in number, and diameter) should be selected to result in this velocity. As is the case with a synthesis reactor, the number dimensions, and distribution of the formations can, if desired, be raised among the trays. The minimum size for e.g. circular perforations is 2 mm, more particularly 2 to 20 mm, although by present preference the range is 4 to 10 mm. The perforations for the transport of the gaseous phase are by preference located in the center of the hydrolyzer tray over 20 to 80% of the surface of the hydrolyzer tray and more particularly over 40 to 60% of the surface.

In the case of urea synthesis reactors or hydrolyzers equipped with the-above-described perforated trays, the number of such trays used in partitioning of the interior volume of a reactor or hydrolyzer is not restricted in number. Present commercial urea plant reactors can use 8–20 trays, and more particularly 8–10 trays, although less than 8 trays, such as 6 or 7, is also possible but is less desired. In general present commercial hydrolyzers in urea plants can have from 10 to 30 trays.

In the preferred embodiments, the tube portion of a liquid riser is substantially perpendicular to the plane defined by a perforated tray.

In principle, a zigzag but somewhat torus liquid flow can, if desired, be induced by staggering the liquid risers between adjacent perforated trays. That is, clockwise, a liquid riser in a perforated tray can be at the 9 position, whereas the next liquid riser in an adjacent perforated tray can be at the 12 or "later" position, and so on, provided that the desired flow velocities are achieved. However, it is presently preferred that the liquid risers between adjacent perforated trays be at opposite ends of a respective tray relative to one another, e.g at the 9 and 3 positions relative to one another.

In the design of these reactors and hydrolyzers, a liquid riser can, if desired, be installed at the perimeter (periphery) of a perforated tray. In this embodiment, still further flexibility in the perforation pattern, distribution, and number is achieved. Depending on design criteria, in principle a reactor or hydrolyzer can include combinations of different liquid riser configurations. For ease of construction or reactor modernizations, it may however, be preferred to standardize on a particular tray structure for a given reactor of hydrolyzer.

The present invention also relates to the modernization of reactors for urea synthesis reactions (or hydrolyzers) in existing plants, and in particular this pertains for urea synthesis at elevated pressure and temperature. Modernization is sometimes referred to as "retrofitting." In modernization, the existing urea reactor or hydrolyzer can be upgraded by installing perforated trays as described hereinabove, whereby urea output and reactant conversion rate for a given energy consumption can be increased on an industrially useful scale. It is presently preferred in modernization to provide an opening for liquid flow at or proximate to the periphery of a perforated reactor tray, and fit, such as by welding, a tube about a said opening to provide a liquid riser as described hereinabove.

The invention is now described further with reference to the accompanying Figures.

FIG. 1 shows a longitudinal cross section view of a part of a reactor with an annular opening (1) for the liquid transport between the perforated reactor trays (2) and the internal wall (3) of the reactor. In the central part of the perforated reactor trays (4) the transport of the gaseous phase takes place in the form of small bubbles which cause a torus-shape circulation in the compartment as indicated by the arrows.

Figure 2:
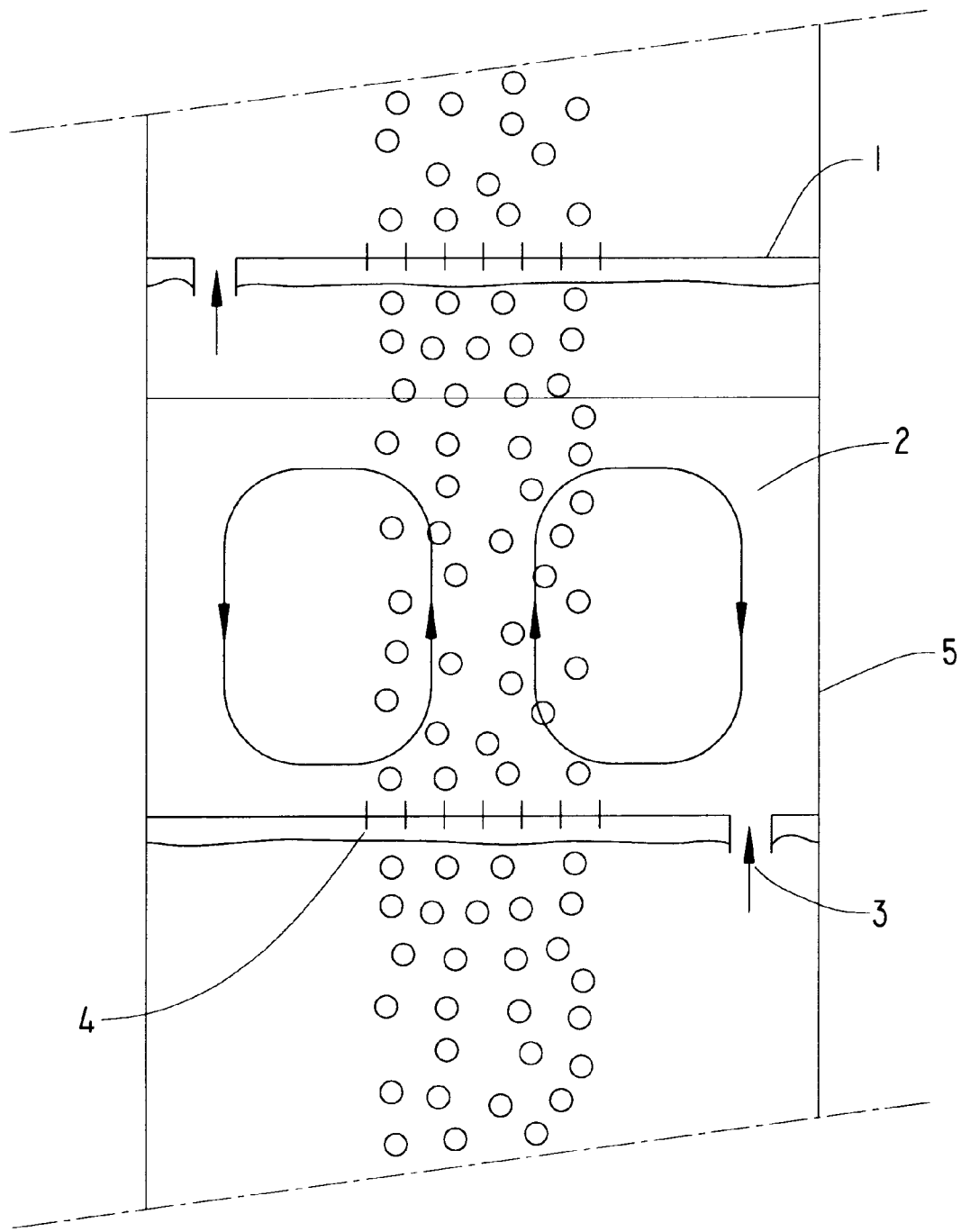
FIG. 2 is a longitudinal cross section view of a part of a urea reactor according to the present invention.

FIG. 2 shows a longitudinal cross section view of a part of a urea synthesis reactor. Perforated reactor trays (1) are positioned within the reactor whereby compartments or zones (2) of substantially equal volume are defined by opposing surfaces of adjacent reactor trays and the inner wall (5) of the reactor. The liquid transport takes place through the liquid risers (3) near the edge of the perforated reactor tray. The liquid risers in two adjacent perforated reactor trays are located opposite the central part of the reactor in order to force the liquid flow to pass through the central part of a reactor zone (2) where the transport of the gaseous flow takes place. Preferably, in a column reactor, the liquid risers can be diametrically opposite one another relative to the vertical axis of the column reactor (or hydrolyzer as the case may be). By having the opposing non-axial alignment of liquid risers, a zigzag flow path of the liquid is created within the reactor (or hydrolyzer) as the liquid flows from partitioned zone (compartment) to partitioned zone. In the central part (4) of the perforated reactor tray the transport of the gaseous phase takes place in the form of small bubbles causing a torus-shape circulation as is indicated by the arrows. Together with the zigzag flow path of the liquid, this torus-shaped circulation avoids the appearance of stagnant zones in a compartment.

The partially cross-sectional view of FIG. 2 does not depict additional more well-known structural components. Among these are means for introducing the reactants, such as ammonia and carbon dioxide, into a lower compartment or zone portions of a vertically disposed column type reactor. The reactor apparatus includes means for withdrawing the product, such as urea-containing product, from an compartment, zone or other partition generally in the upper internal volume of the reactors. The means for introducing reactants and the means for withdrawing the product are known to those skilled in the art.

Figure 3:
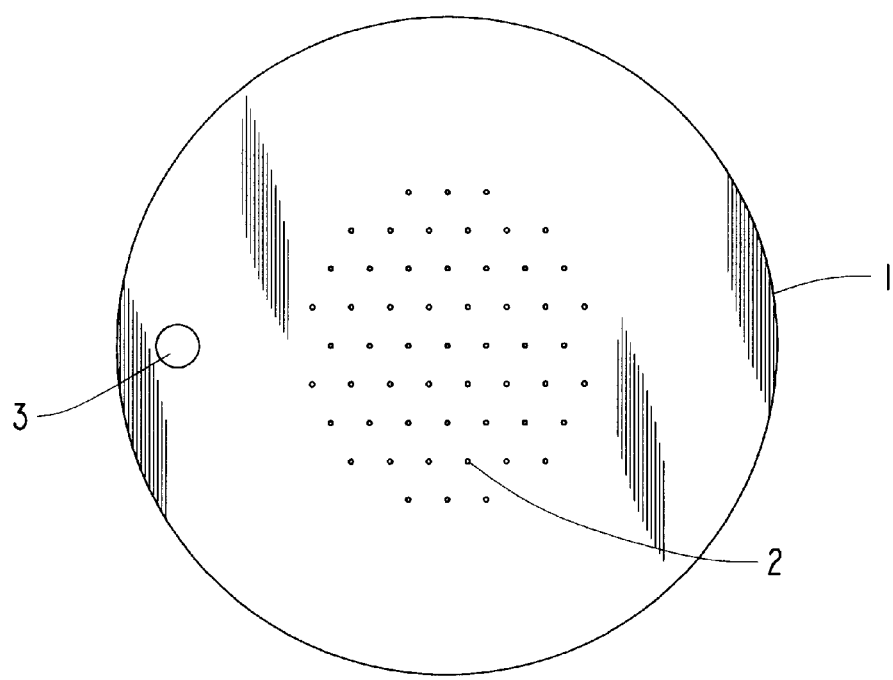
FIG. 3 shows a representative, but specific, form of tray perforation useful in a reactor according to the present invention.

FIG. 3 depicts a specific form of a tray (1) having a plurality of perforations (2) for the transport of the gaseous phase and at least one tube (3) for liquid transport which can be used to carry out the process of the present invention, or for modernizing an existing reactor.

Figure 4:
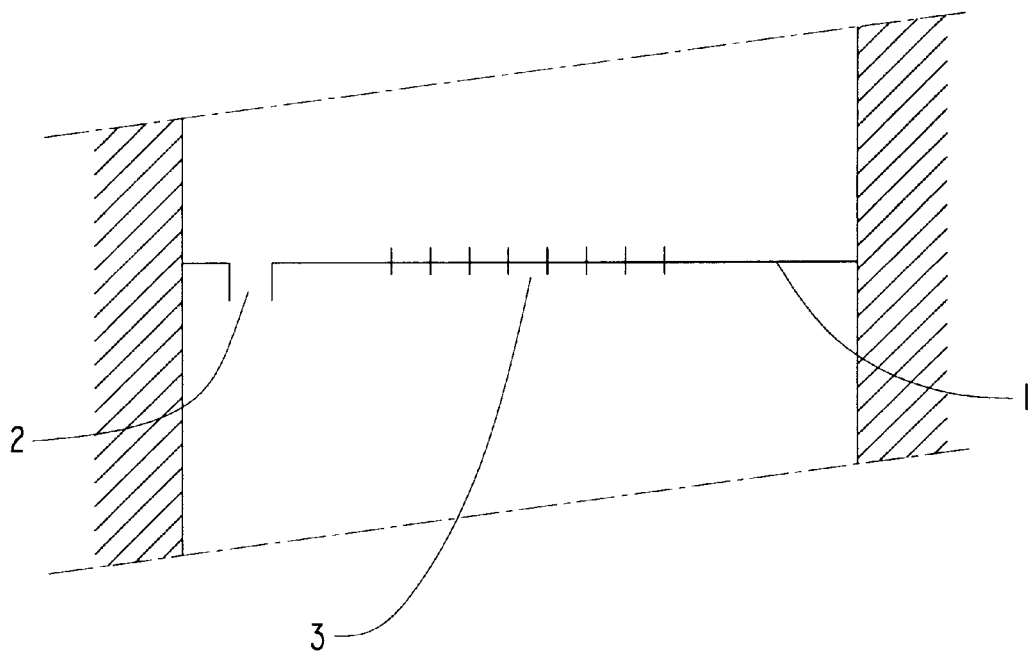
FIG. 4 shows a representative liquid riser equipped with a hollow tube on the underside of a perforated reactor tray.

FIG. 4 shows a representative reactor tray (1) with tube (2) and perforations for the gaseous phase (3) useful in a reactor according to the present invention.

Figure 5:
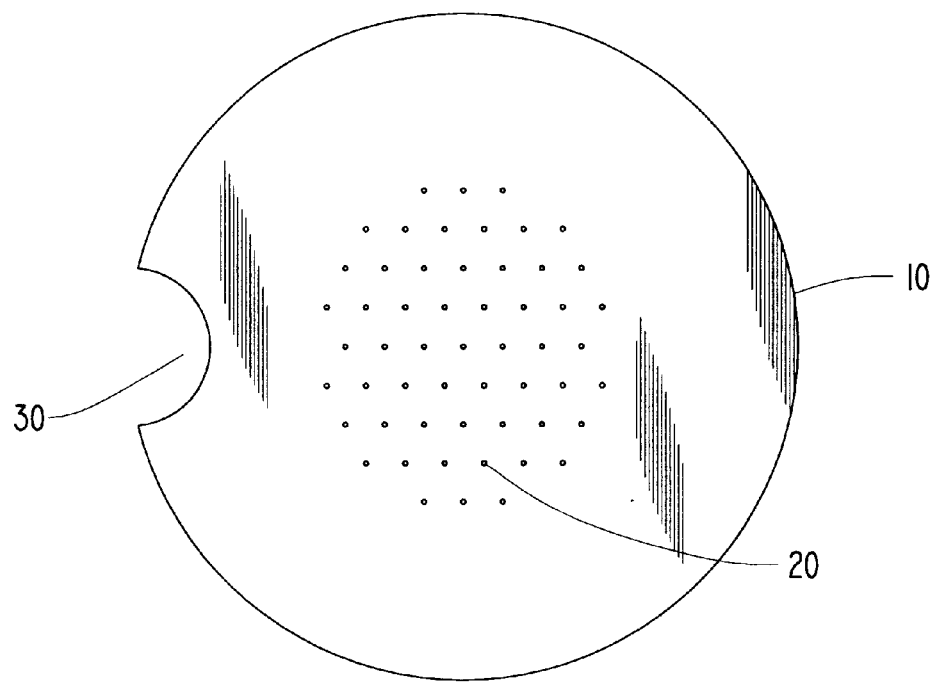
FIGS. 5 and 6 show a top and side view, respectively, a liquid riser, on the outer edge of a perforated tray according to the present invention.
Figure 6:
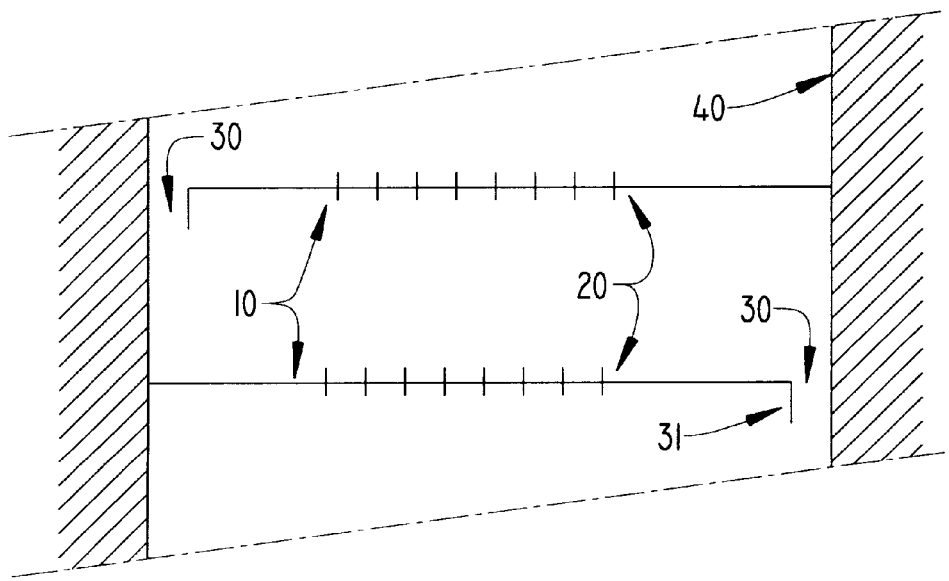

FIGS. 5 and 6 show another embodiment of a perforated tray (10). In the FIG. 5 top view, tray (10) has perforations (20) in a central region which are spaced apart by a non-perforated region from a liquid riser 30 located at the edge of tray 10. As illustrated, liquid riser 30 has an arcuately shaped opening, and is should be understood that this is only one embodiment. In the FIG. 6 cross-sectional side view, the reactor or hydrolyzer side wall 40 together with partial tube 31 forms a liquid riser 30. Although not shown, in FIG. 6 the partial tube 31 has a top edge which is integral with and conforms to the contour of the opening of liquid riser 30 depicted in FIG. 5, and as illustrated has side edges which are substantially perpendicular to perforated plate 10, which side edges terminate at or close to side wall 40 of the hydrolyzer or reactor to thereby form the liquid riser. Perforations 20 are shown in FIG. 6.

We have discovered that with an improved reactor according to the present invention the conversion of carbon dioxide into urea has been increased from approximately 60% to approximately 63.5%. In practical terms, this increase is particularly significant. It results in a larger production capacity and a lower energy consumption compared with reactors as described in FIG. 1. For a new urea plant this means that a smaller reactor can be installed but the same output and the same energy consumption can be reached. An advantage for a modernized existing plant is the reduction in energy consumption and an increase in urea production can also be achieved when reactors are retrofitted with the reactor trays provided with a tube described herein.

The present inventions are described further in the following non-limiting examples.

EXAMPLES

Comparative Example A

A urea reactor in a commercial urea plant operating under the Stamicarbon Carbondioxide Stripping Process (See European Chemical News Urea Supplement; Jan. 17, 1969; pages 17–20, the complete disclosure of which is incorporated herein by reference) was provided with 10 reactor trays of the type given in FIG. 1. This urea reactor was operated under the following conditions: reactor top temperature 187° C., and at a reactor pressure 148 bar.

Under these conditions, the conversion of carbondioxide to urea in the liquid mixture leaving the reactor was 61.7 mol %; whereas the conversion of ammonia to urea in this liquid was 39.2 mol %. In the downstream of the reactor installed carbondioxide stripper of the Carbondioxide Stripping Process, was 862 kg steam required per ton of produced urea, to separate the majority of non-converted ammonia and carbondioxide from the urea/water mixture.

EXAMPLE I

In the same urea plant as in Comparative Example A, the 10 reactor trays were modified into 10 reactor trays as indicated in FIGS. 2, 3 and 4. The urea reactor was again operated under the following conditions: a reactor top temperature 187° C., and a reactor pressure 148 bar.

The urea output of the urea plant increased by 6%. At this higher capacity the conversion of carbondioxide in urea was 62.8 mol %, the conversion of ammonia to urea was 39.9 mol % steam consumption in the stripper was 824 Kg/ton urea while maintaining the same degree of separation of non-converted ammonia and carbon dioxide.

EXAMPLE II

In the same urea plant as in Example 1 the urea reactor was again operated under the same temperature and pressure.

The urea output was maintained on the same level as in the Comparative Example A. While operating the urea plant under these conditions the following results were obtained: a conversion of carbondioxide to urea was >63 mol %, the conversion of ammonia to urea > was 40 mol %, the steam consumption in the stripper was <800 Kg/ton urea, while maintaining the same degree of separation of non-converted ammonia and carbondioxide.

What is claimed is:

1. A process for synthesizing urea at an elevated temperature and pressure, comprising:

introducing ammonia and carbon dioxide into a reactor, resulting in the formation of a gaseous phase and a liquid phase, wherein the reactor has an internal volume and comprises;
a plurality of perforated reactor trays disposed at least substantially transversely across the internal volume thereby defining a plurality of zones, wherein the perforated reactor trays have a center and a periphery, said perforated reactor trays comprising,
a perforated region extending over 20–80% of the tray surface proximate with the center of the tray, and
at least one liquid riser located proximate with the periphery of the tray and not in axial alignment with the liquid riser in adjacent trays, wherein the liquid riser comprises a tube having a height of 100 to 300 mm located on and depending from an underside of the tray;

maintaining a gaseous phase velocity of 2.5–5 m/sec in the perforations of the perforated reactor trays;

wherein the velocity of the liquid phase in the liquid riser is between 0.1 to 0.6 m/sec; and withdrawing a urea-containing product from said internal volume.

2. The process according to claim 1, wherein the velocity of the gaseous phase is about 3 m/sec.

3. The process according to claim 1, wherein the size of the perforations in the trays is in the range of 2 to 20 mm.

4. The process according to claim 1, wherein the temperature in the reactor is between 160°–200° C.

5. The process according to claim 1, wherein the pressure is between 120 and 175 bar.

6. The process according to claim 1, wherein the reactor is constructed by retrofitting an existing reactor.

7. The process according to claim 6, wherein said retrofitting includes installing said perforated reactor trays.

8. The process according to claim 6, wherein said retrofitting includes fitting at least one said liquid riser to at least one of said perforated reactor trays.

* * * * *